US006642020B2

United States Patent
Sánchez-Ferrer et al.

(10) Patent No.: US 6,642,020 B2
(45) Date of Patent: Nov. 4, 2003

(54) PROCESS FOR PREPARING CEPHALOSPORIN DERIVATIVES

(75) Inventors: Álvaro Sánchez-Ferrer, Murcia (ES); José Aniceto López-Más, Alicante (ES); Francisco Garcia-Carmona, Murcia (ES)

(73) Assignee: Bioferma Murcia S.A., Murcia (ES)

( * ) Notice: Subject to any disclaimer, the term of this patent is extended or adjusted under 35 U.S.C. 154(b) by 0 days.

(21) Appl. No.: 10/125,554

(22) Filed: Apr. 19, 2002

(65) Prior Publication Data
US 2003/0073156 A1 Apr. 17, 2003

(30) Foreign Application Priority Data

| Apr. 19, 2001 | (EP) | 01201426 |
| May 9, 2001 | (EP) | 01201699 |
| May 9, 2001 | (EP) | 01201718 |
| Nov. 30, 2001 | (IE) | 2001/1025 |
| Nov. 30, 2001 | (IE) | 2001/1024 |

(51) Int. Cl.[7] .................... C12P 35/00; C12P 35/06
(52) U.S. Cl. ................ 435/47; 435/49; 540/224; 540/229
(58) Field of Search ............. 435/47, 49; 540/224, 540/229

(56) References Cited

U.S. PATENT DOCUMENTS

| 3,278,531 A | 10/1966 | Cox et al. ............ 260/243 |
| 3,367,933 A | 2/1968 | Eardley et al. ........ 260/243 |
| 3,502,665 A | 3/1970 | Wetherill et al. ...... 260/243 |
| 3,516,997 A | 6/1970 | Takano et al. ......... 260/243 |
| 3,647,788 A | 3/1972 | Clark et al. .......... 260/243 |
| 3,872,115 A | 3/1975 | Sugimoto et al. ...... 260/243 |
| 3,878,204 A | 4/1975 | Ochiai et al. ......... 260/243 |
| 3,892,737 A | 7/1975 | Ochiai et al. ......... 260/243 |
| 3,954,745 A | 5/1976 | Jackson et al. ........ 260/243 |
| 3,960,662 A | 6/1976 | Matsuda et al. ........ 195/29 |
| 3,979,383 A | 9/1976 | Wild .................. 260/243 |
| 4,036,833 A * | 7/1977 | Ishimaru et al. ....... 424/246 |
| 4,115,645 A | 9/1978 | Jackson et al. ........ 544/20 |
| 4,145,539 A * | 3/1979 | Hattori et al. ........ 544/20 |
| 4,317,907 A | 3/1982 | Saikawa et al. ........ 544/21 |
| 4,379,924 A * | 4/1983 | Numata et al. ......... 424/246 |
| 4,774,179 A | 9/1988 | Ichikawa et al. ....... 435/51 |
| 4,981,789 A * | 1/1991 | Lein .................. 435/51 |
| 5,104,800 A * | 4/1992 | Crawford et al. ....... 435/47 |
| 5,296,358 A | 3/1994 | Battistel et al. ...... 435/49 |
| 5,387,679 A | 2/1995 | Sogli et al. .......... 540/226 |
| 5,599,702 A | 2/1997 | Sauber ................ 435/181 |
| 6,395,507 B1 * | 5/2002 | Bongs et al. .......... 435/47 |

FOREIGN PATENT DOCUMENTS

| CH | 520709 | 5/1972 |
| DE | 1939341 | 2/1970 |
| DE | 1953861 | 5/1971 |
| DE | 2056983 | 6/1971 |
| DE | 2332045 | 1/1974 |
| DE | 2626026 | 12/1977 |
| EP | 0167651 B1 | 9/1989 |
| EP | 0436355 A2 | 7/1991 |
| EP | 0492495 A2 | 7/1992 |
| EP | 0283218 B1 | 7/1993 |
| EP | 0583817 A2 | 2/1994 |

(List continued on next page.)

OTHER PUBLICATIONS

Parmar et al, Critical Reviews in Biotechnology, 18 (1), 1998, pp. 1–2, Recent Trends in Enzymatic Conversion of . . . .

Conlon et al, Biotechnology & Bioengineering, vol. 46, 1995, pp. 510–513, Two–Step Immobilized Enzyme Conversion of . . . .

(List continued on next page.)

Primary Examiner—Herbert J. Lilling
(74) Attorney, Agent, or Firm—Jacobson Holman PLLC

(57) ABSTRACT

An enzymatic process for preparing 3-thiolated 7-aminocephalosporanic acid derivatives comprises the steps of enzymatically converting a 3-thiolated cephalosporin C of the formula I:

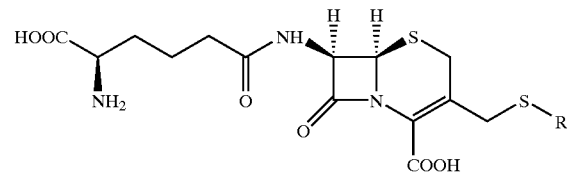

(I)

to form a 3-thiolated-glutaryl-7-ACA of the formula II

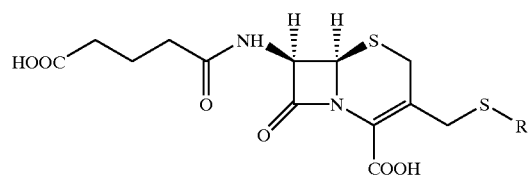

(II)

and enzymatically converting a compound of formula II to form a 3-thiolated-7-ACA of the formula III

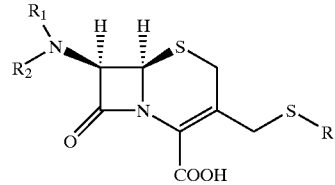

(III)

wherein R is a heterocyclic group comprising at least one nitrogen atom and $R_1$ and $R_2$ are both hydrogen atoms or one of them is a hydrogen atom and the other is an acyl donor.

19 Claims, No Drawings

FOREIGN PATENT DOCUMENTS

| | | |
|---|---|---|
| EP | 0364275 B1 | 5/1995 |
| EP | 0496993 B1 | 5/1996 |
| EP | 0517200 B1 | 8/1996 |
| EP | 0846695 A1 | 6/1998 |
| EP | 1188838 A1 | 3/2002 |
| FR | 2241557 | 3/1975 |
| GB | 1101422 | 1/1968 |
| GB | 1239814 | 7/1971 |
| GB | 1272769 | 5/1972 |
| GB | 1295841 | 11/1972 |
| GB | 1385685 | 2/1975 |
| GB | 1400804 | 7/1975 |
| GB | 1438800 | 6/1976 |
| GB | 1565053 | 4/1980 |
| GB | 1566515 | 4/1980 |
| JP | 55-139327 | 10/1980 |
| JP | 56-164194 | 12/1981 |
| JP | 59-170095 | 9/1984 |
| JP | 2-270883 | 11/1990 |
| WO | WO90/12110 | 10/1990 |
| WO | WO93/02085 | 2/1993 |
| WO | WO95/12680 | 5/1995 |
| WO | WO95/16773 | 6/1995 |
| WO | WO95/35020 | 12/1995 |
| WO | WO96/16174 | 5/1996 |
| WO | WO00/78989 | 12/2000 |

OTHER PUBLICATIONS

Won et al, Applied Biochemistry and Biotechnology, Vol, 69, 1998, pp. 1–9, The Effect of 2–Mercapto–5–Methyl–1, 3,4–Thiadiazole . . . .

Hannah et al, Jour of Medicinal Chemistry, vol. 25, No. 4, 1982, pp. 457–469, Quaternary Heterocyclylamino β–Lactams: A . . . .

Nomura et al, Jour of Medicinal Chemistry, vol. 17, No. 12, 1974 Semisynthetic β–Lactam Antibiotics 6. Sulfocephalosporins and . . . .

Cocker et al, Jour of Chemical Society, 1965, pp. 5015–5031, Cephalosporanic Acids. Part II. Displacement of the . . . .

Justiz et al, Jour Organic Chemistry 62, 1997, pp. 9099–9061, One–Pot Chemoenzymatic Synthesis of 3'–Functionalized . . . .

The Merck Index on CD–ROM, Version 12:2, 1997, Merck & Co. Inc., XP002177921, 4 pgs.

Patent Abstracts of Japan, vol. 5, No. 152, Sep. 25, 1981 & JP 56 085298 A (Asahi Chem. Ind. Co.).

Patent Abstracts of Japan, vol. 11, No. 322, Oct. 20, 1987 & JP 62 107798 A (Asahi Chem. Ind. Co.), May 19, 1987.

Baldwin et al, Bioorg. Med. Chem. Lett., vol. 5, No. 21, 1995, pp. 2507–2512, Cleavage of the 5–amino–5–carboxyl–. . . .

Database Crossfire Beilstein, Accession No. 1198450 XP002211689 & abstract DE 21 37 386 A (Takeda Chem. Ind.), May 31, 1972.

Database Crossfire Beilstein, Accession No. 599207 XP002211690 & abstract CH 601 312 A (Fujisawa Pharm.), Jul. 14, 1978.

Database Crossfire Beilstein, Accession No. 600138 XP002211691 & abstract DE 22 39 947 A (Takeda Chem. Ind.), Mar. 15, 1973.

Database Crossfire Beilstein, Accession No. 1097400 . . . , XP002211692, abstract ZA 6 802 695 A (Fujisawa Pharm. Co.), 1967.

Chemical Abstracts, vol. 80, No. 13, Apr. 1, 1974 & JP 48 075587 A (Fujisawa Pharmaceutical Co., Ltd,), Oct. 11, 1973.

Chemical Abstracts, vol. 86, No. 15, Apr. 11, 1977 & JP 51 088694 A (Toyo Jozo Co., Ltd.), Aug. 3, 1976.

Database Crossfire Beilstein, Accession No. 1063938 XP002211693 & abstract JP 04 638007 A (Sugimoto Keiti et al), 1976.

Database Crossfire Beilstein, Accession No. 1063270 . . . , XP002211694, abstract NL 6 411 521 A (Glaxo Group), Apr. 5, 1965.

* cited by examiner

PROCESS FOR PREPARING CEPHALOSPORIN DERIVATIVES

The invention relates to a process for the preparation of 3-cephalosporin C derivatives which are used in the preparation of β-lactam antibiotics. In particular, the invention relates to a process for the preparation of 3-thiolated derivatives of 3-acetoxy-methyl-7-amino-ceph-3-em-carboxylic acid.

BACKGROUND

All cephalosporins used in therapeutic applications are semi-synthetic and are produced by modifying the basic β-lactam structure in the material obtained from a fermentation broth of *Acremonium chrysogenum* or, after chemical transformation, from the products obtained from fermentation broths of *Penicillium chrysogenum* using different precursors.

Typically, cephalosporin C [3-acetoxymethyl-7-(D-5-amino-5-carboxy pentan amido)-ceph-3-em-4-carboxylic acid] is converted into 3-acetoxymethyl-7-amino-ceph-3-em-carboxylic acid, usually known as 7-amino cephalosporanic acid (7-ACA), by removing the lateral aminoadipic chain of the β-lactam ring. The 7-ACA is purified and crystallised, and is then used as starting material for subsequent modifications at the 7- and 3-position. 7-ACA is the base building block used in the synthesis of many important semi-synthetic cepahalosporin antibiotics that are of current interest in the biopharmaceutical industry.

3-thiomethyl Cephalosporin C derivatives have been disclosed in U.S. Pat. Nos. 3,278,531; 3,516,997; 3,647,788; GB 1,400,804; GB 1,565,053 and GB 1,566,515. A few examples of 3'-thiomethyl glutaryl 7-ACA derivatives are described in WO-A-9535020 and EP 0846695.

7-ACA is the most widely used intermediate for reaction with heterocyclic thiols as it can be obtained either chemically or enzymatically on an industrial scale. This has been disclosed in several patents including U.S. Pat. Nos. 3,502,665; 3,954,745; 3,516,997; 3,979,383; 4,115,645; 4,317,907; 5,387,679; JP 55,139,327; EP 0167651 and WO-A-9302085.

U.S. Pat. No. 5,387,679 describes the reaction of 7-amino cephalosporanic acid with 2-mercapto-5-methyl-1,3,4-thiadiazole (MMTD) in the presence of sodium bicarbonate in aqueous acetone, at pH 6–7. A yield of about 60–65% is achieved.

In U.S. Pat. No. 4,317,907, the yield of the above reaction in anhydrous medium was increased to about 86% when acetic acid or nitromethanol was used as a solvent, in the presence of boron trifluoride or boron trifluoride etherate. However the purity is low, 80% max, as it contains unreacted 7-ACA and degradation products. In WO-A-9302085 the use of dialkyl carbonate in the presence of a dialkyl carbonate trifluoride complex and an aliphatic acid increased the yield to a maximum of 89%. However, WO-A-9302085 shows the problems associated with using toxic and very expensive gas such as $BF_3$ and the handling of waste effluent which contains borides and fluoroborides.

The deacylation of cephalosporin C, i.e., the elimination of the 7'-lateral side chain, is usually carried out chemically, for example using nitrosyl chloride in formic acid in the presence of acetonitrile (U.S. Pat. No. 3,367,933). Another method of deacylation involves the protection of the carboxyl group of aminopenteanoic chain, reaction with phosphorus pentachloride at –55° C. and subsequent hydrolysis at low temperature with a mixture of water and methanol (BE 718,824).

These known methods must generally be carried out at low temperatures, and require the use of costly and toxic solvents or reagents, consequently they may have a serious environmental impact. In addition, because of the chemical instability of the β-lactam nucleus and the reactivity of the groups present in positions 3 and 7 of the ring, special reaction conditions must be applied, which makes the process on an industrial scale complex.

To overcome the drawbacks of the chemical route to 7-ACA, alternative enzymatic cleavage of cephalosporin C has been described. Direct one-step removal of the lateral 7-aminoadipic side-chain of cephalosporin C is possible by using specific cephalosporin acylases (FR 2,241,557; U.S. Pat. No. 4,774,179; EP 283,248; WO-A-9512680; WO-A-9616174). These processes, however, are often not reproducible and are characterised by low yields and lengthy reaction times as described in U.S. Pat. No. 5,296,358. No industrial application of this technology (single-step conversion of cephalosporin C to 7-ACA) has been reported at this time (Parmar et al, Crit. Rev. Biotechnol. 18, 1, 1998).

On the other hand, processes that transform the cephalosporin C into 7-ACA by means of two enzymatic steps are important from an industrial point of view. The first stage consists of using a D-amino acid oxidase (E.C. 1.4.3.3, hereinbelow indicated as DAAO) from different sources (*Trigonopsis variabilis*, GB 1,272,769; *Rhodotorula gracilis*, EP 0,517,200; or *Fusarium solari* M-0718, EP 0,364,275). DAAO oxidises the lateral D-5-amidocarboxypentanoyl chain of cephalosporin C in the presence of molecular oxygen, to produce 7β-(5-carboxy-5-oxopentamido)-ceph-3-em-carboxylic acid (or α-ketoadipyl-7-aminocephalo-sporanic acid, hereinbelow indicated as α-ketoadipyl-7-ACA) and hydrogen peroxide, which chemically decarboxylate the α-ketoadipyl-7-ACA to 7β-(4-carboxy butanamido)-ceph-3-em-4-carboxylic acid (or glutaryl-7-aminocephalosporanic acid, hereinbelow indicated as GL-7-ACA).

In a second stage, a specific acylase for GL-7-ACA, glutaryl-7-ACA acylase (E.C. 3.5.1.3), is used, for example that of a Pseudomonas type microorganism (U.S. Pat. No. 3,960,662, EP 0496993) over expressed in *E. coli*, which deacylates the GL-7-ACA into 7-ACA.

This two-step enzymatic process for obtaining 7-ACA has been used on an industrial scale (Conlon et al. Biotechnol. Bioeng. 46, 510, 1995).

An environmental-friendly alternative to produce 3'-heterocyclic thiomethyl cephasporanic acid derivatives was disclosed in EP 0846695. Chemical nucleophilic displacement of the 3-position of glutaryl-7-ACA in aqueous medium is followed by an enzymatic transformation of the 3'glutaryl-7-ACA-derivative by using the enzyme glutaryl-7-ACA acylase. The quantity of the derivative is about 65% with no environmental impact. This procedure can be defined as an enzymatic-chemical-enzymatic (ECE) process, since the isolated GL-7-ACA comes from a bioconversion of solubilised cephalosporin C, then GL-7-ACA is reacted with the heterocyclic thiols and finally the 3-heterocyclic thio-derivative is enzymated with GL-7-ACA acylase. The problem with this method is the need to isolate GL-7-ACA, which given its high water solubility, is technically difficult and expensive, as described in WO-A-9535020.

An additional problem is that the enzyme is only reusable for a few cycles. In fact no more than three cycles are described with 5-mercaptotriazol and MMTD, where the residual amount of MMTD after crystallisation is 2.8 mg/ml.

The other two thiols used as examples are only used in one cycle due to the high amounts of the thiols remaining in solution. This is the case with 5-mercapto-1-methyltetrazole (MMTZ) or 2,5-dihydro-3-mercapto-2-methyl-5,6-dioxo-1,2,4-triazine (TTZ), which are very soluble in water and not removable by decreasing the pH. This poisoning effect of the thiol has also been described for MMTD on Penicillin G Amidase from *E. coli* CFC-04017 (Won et al, App. Biochem. Biotech. 69, 1, 1998) during the enzymatic synthesis of cefazolin. To overcome this inhibitory effect the molar ratio of MMTD/7-ACA is decreased to 1.2:1 in order to extend the lifetime of the enzyme. This low molar ratio reduces the yield of the 3-thio derivative and avoids the use of the other published process on the chemo-enzymatic synthesis of 3-modified cephalosporins, in which an enzymatic-enzymatic-chemical process (EEC) is proposed, using D-amino acid oxidase—glutaryl-7-ACA acylase and a chemical reaction with heterocyclic thiols (Jistiz et al., J. Org. Chem. 62, 9099, 1997).

There is therefore a need for an improved process for preparing 3-cephalosporin C derivatives.

STATEMENTS OF INVENTION

According to the invention there is provided an enzymatic process for preparing 3-thiolated 7-aminocephalosporanic acid derivatives comprising the steps:

enzymatically converting a 3-thiolated cephalosporin C of the formula I:

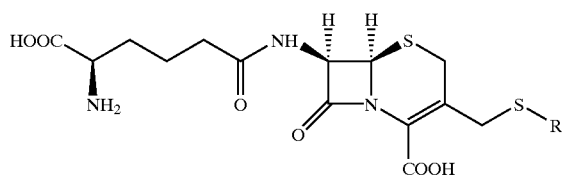

(I)

to form a 3-thiolated -glutaryl-7-ACA of the formula II

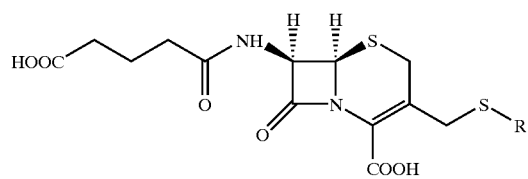

(II)

and enzymatically converting a compound of formula II to form a 3-thiolated-7-ACA of the formula III

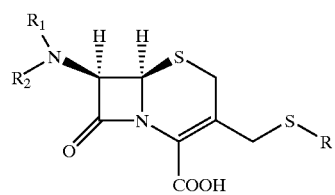

(III)

wherein R is a heterocyclic group comprising at least one nitrogen atom and $R_1$ and $R_2$ are both hydrogen atoms or one of them is a hydrogen atom and the other is an acyl donor.

Preferably the 3-thiolated cephalosporin C of formula I is converted into a 3-thiolated-glutaryl-7-ACA of the formula II by:

reacting a compound of formula I with immobilised D-Amino acid oxidase in the presence of molecular oxygen;

separating the supported enzyme from the aqueous reaction mixture; and adding hydrogen peroxide to convert the 3-thiolated-α-ketoadipyl cephalosporanic acid into a compound of formula II.

In one embodiment of the invention the compound of formula I is reacted with immobilised D-Amino acid oxidase at a pressure of about 2 bar absolute, a pH of from 6.0 to 8.0, and a temperature of from 20° C. to 30° C. for a period of from 0.5 to 3 hours.

Preferably the process includes the step of washing the supported enzyme with a concentrated salt solution and adding hydrogen peroxide preferably in an amount equivalent to 30 to 50 ppm to the solution thus formed.

Most preferably the process comprises the step of eliminating excess hydrogen peroxide from the solution, preferably by adding a catalyst to the solution.

In one embodiment of the invention the excess hydrogen peroxide is removed by adding catalase to the solution. Preferably a compound of formula II is converted into a compound of formula III by contacting a compound of formula II with immobilised glutaryl-7-ACA acylase. Most preferably the reaction to form a compound of formula III from a compound of formula II is carried out at ambient pressure, at a pH of from 6.0 to 8.5 and at a temperature of from 20° C. to 35° C., for a period of from 0.5 to 3 hours under an inert atmosphere.

In one embodiment of the invention the compound of formula III is precipitated by acidifying the reaction medium and the precipitate thus formed is subsequently washed and dried.

In another embodiment of the invention the enzymes are immobilised using a suitable cross-linker agent in a suitable solid support. Preferably the enzymes are in the form of crystals of a size suitable for use as a biocatalyst. Most preferably the enzymatic processes are carried out while maintaining the enzyme in dispersion in an aqueous substrate solution.

In one embodiment of the invention the or each enzymatic process is carried out in a column.

Preferably the process includes the step of recovering the enzyme for reuse.

In one embodiment of the invention crystallisation of a compound of formula III is carried out at an acidic pH.

One aspect of the invention provides a process of the invention wherein the enzymatic conversion of a 3 thiolated cephalosporin C of the formula I to form a 3 thiolated-7-ACA of the formula III is carried out in one step.

In one embodiment of the invention compounds of formula I are in a solid form or in the form of a non-toxic salt thereof. Non-toxic salts may include cations used in the crystallisation of cephalosporin C which are non-toxic for humans such as zinc salts.

The invention also provides a process for the preparation of Cephalosporin C antibiotics and derivatives thereof comprising forming a compound of formula III and subsequent enzymation. Preferably the antibiotic is selected from any one or more of cefazolin, cefazedone, cefoperazone, cefamandol, cefatriazine, cefotiam or ceftriaxone.

In one embodiment of the invention the enzymatic process for preparing 3-thiolated 7-aminocephalosporanic acid derivatives comprises the steps:

reacting Cephalosporin C with a thiol compound of the general Formula IV

R—SH (IV)

wherein R is a heterocyclic group comprising at least one nitrogen atom, to form a compound of formula I and, after formation of the compound of formula I removing excess thiol of Formula IV.

Preferably the excess thiol is removed by adsorption on an anion exchange resin. Most preferably the anion exchange resin is a microporous resin having a cross-linked acrylic copolymer structure. Preferably the anion exchange resin comprises an 8% cross-linking containing functional thialkyl benzyl ammonium group. The resin may be in the chloride, hydroxy, phosphate or acetate cycle.

In one embodiment of the invention the excess thiol is removed by crystallisation. Preferably crystallisation is carried out at an acidic pH. Most preferably the excess thiol is removed by crystallisation followed by adsorption on an anion exchange resin.

In one embodiment of the invention the cephalosporin C is in an aqueous medium.

In another embodiment of the invention the cephalosporin C is in the form of a concentrated cephalosporin C solution obtained from solid cephalosporin C or from a direct or purified cephalosporin C broth. The cephalosporin C may be in the form of a concentrated cephalosporin C solution or a concentrated cephalosporin C broth.

In one embodiment of the invention the reaction process is carried out at a pH of between 5.5 and 8.0, at a temperature of from 60° C. to 80° C., for a period of from 1 to 12 hours. Preferably the reaction is carried out at a pH of approximately 6.0 and at a temperature of approximately 65° C. Most preferably the thiol compound is present in an amount of between 1 and 5 mol/mol of cephalosporin C.

R may be a heterocyclic group comprising at least one nitrogen atom and optionally a sulphur or oxygen atom. Preferably R is a heterocyclic group selected from any one or more of the group comprising thienyl, diazolyl, tetrazolyl, thiazolyl, triazinyl, oxazolyl, oxadiazolyl, pyridyl, pirimidinyl, benzo thiazolyl, benzimidazolyl, benzoxazolyl, or any derivative thereof, preferably 5-methyl-1,3,4-thiadiazol-2-yl, 1-methyl-1H-tetrazol-5-yl or 1,2,5,6-tetrahydro-2-methyl-5,6-dioxo-1,2,4-triazin-3-yl.

In one embodiment of the invention compounds of formula I are in a solid form or in the form of a non-toxic salt thereof.

The invention provides a compound of the formula:

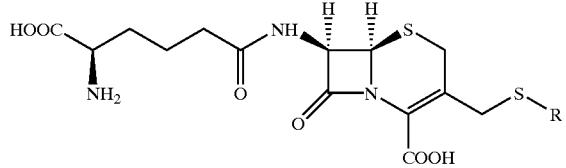

wherein R is a heterocyclic group comprising at least one nitrogen atom, obtained by a process of the invention.

The invention also provides a compound of the formula:

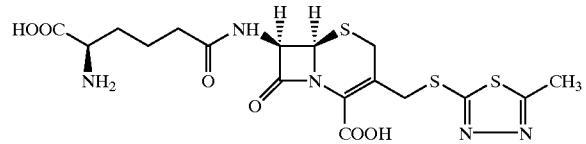

wherein in formula I R is 5-methyl-1,3,4-thiadiazol-2-yl.

The invention provides a compound of the formula:

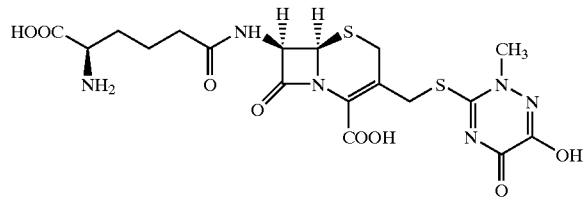

wherein in formula I, R is 1,2,5,6-tetrahydro-2-methyl-5,6-dioxo-1,2,4-triazin-3-yl.

The invention also provides a process for the preparation of cephalosporin C antibiotics and derivatives thereof comprising forming a compound of formula I as hereinbefore defined and subsequent enzymation of the compound of formula I. Preferably the antibiotic is selected from any one or more of cefazolin, cefazedone, cefoperazone, cefamandol, cefatriazine, cefotiam and ceftriaxone.

DETAILED DESCRIPTION

We have found that a chemical-enzymatic-enzymatic process (CEE), in which cephalosporin C in solution is first reacted with a heterocyclic thiol before enzymatic removal of the 7-position side chain, provides an improved process for preparing 3-cephalosporin C derivatives.

The process of the invention can be represented as follows.

First stage: Immobilisec D-amino acid oxidase in the presence of $O_2$

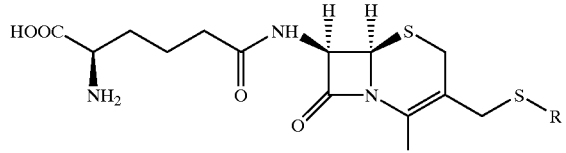

(I)
3-thiolated cephalosporin C (T'X'C)

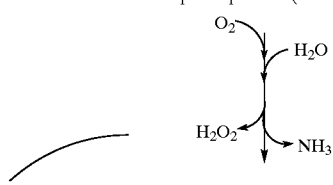

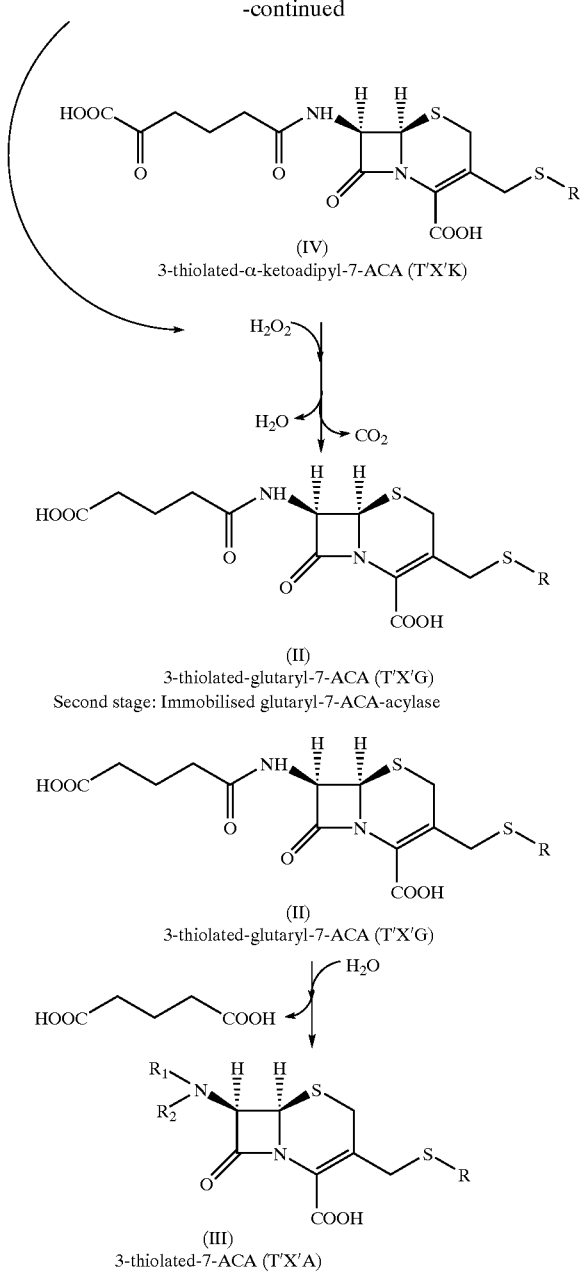

where R is a heterocyclic comprising at least a nitrogen atom with or without a sulphur or oxygen, such as thienyl, diazolyl, triazinyl, triazolyl, tetrazolyl, thiazolyl, thiadiazolyl, thiatriazolyl, oxazolyl, oxadiazolyl, pyridyl, pyrimidinyl, benzothiazolyl, benzimidazolyl, benzoxazolyl or their substituted derivatives in any of the possible positions of the above mentioned heterocyclic structure, available for substitution.

The enzymatic conversion of the compound I into the 3-thiolated glutaryl-7-ACA (compound II) is carried out in aqueous solution with a pH of about 6.5 to 8.0, preferably at pH 7.0. This avoids the problem of increasing instability of cephalosporanic compounds at pH levels above 8. The reaction temperature can be operated from 15° C. to 35° C., and is normally fixed to 20° C. The concentration of 3-thiolated cephalosporin C derivatives can vary from 35–150 mM.

Molecular oxygen acts as a co-substrate for the oxidative deamination. This is sparged into the reaction solution through a bottom diffuser at a flow rate from 0.01 to 1 vol/vol of solution/minute, preferably at 0.1 vvm under a suitable mechanical stirring. It will be apparent to a person skilled in the art that the rate of stirring may vary according to a wide range of design parameters and reaction characteristics. Ordinarily, the stirring would be in the range 20–500 rpm. This design of bioreactor is preferred to a percolation column containing the immobilised crystalline enzyme, in which it is difficult to obtain adequate transfer of oxygen, thus reducing the final yield of 3-thiolated glutaryl-7-ACA.

The time required for complete transformation is of the order of 0.5 to 3 hours, depending on the operating conditions, but is typically approximately 1 hour.

The conversion from compound of formula I to compound of formula II is high, and normally about 98% with a product yield of 95%. At the end of the reaction, the reaction solution still contains some un-degraded intermediate compounds of formula IV, which are converted to compounds of formula II using external hydrogen peroxide. In addition, some compounds of formula II can remain bound to the resin in which the enzymes are immobilised.

To reduce the impact of these potential losses, the reactor solution is discharged with overpressure to a holding tank and the enzyme is washed with a 100 mM phosphate buffer at a pH of 7.0. Other buffer solutions with similar characteristics may be used. This buffer wash is combined with the reaction solution, which mixture is then titrated with hydrogen peroxide, final concentration in solution 30–50 ppm for 30–50 minutes at about 25° C., preferably to 35 ppm for 30 minutes.

The excess of $H_2O_2$ is eliminated before passing to the next step by a suitable enzyme, such as catalase, a suitable reducing agent such as pyruvic acid, alkaline sulphites or any other suitable catalyst in soluble or immobilised form. The enzymatic removal of $H_2O_2$ is preferred in this invention to preserve the quality and purity of the final product.

By the above treatments, the final compound (II) yield was 97–98% which is 3% higher than that described in EP 0496993 for the conversion of unmodified cephalosporin C into glutaryl-7-ACA.

The final solution after $H_2O_2$ titration is adjusted to a pH of approximately 7.5 to 8.5, preferably to pH 8.0 with a concentrated organic or inorganic base, such as ammonia, before being transferred to the second bioreactor charged with a suitable wet immobilised or crystalline glutaryl-7-ACA acylase preparation. Commercially available preparations, such as are available from Roche Molecular Biochemicals are suitable for the purpose. The pH is maintained by dosing the reaction with the same organic or inorganic base as above described by using an autotitrator fixed at about pH 8.0. The operating temperature may be from about 15° C. to 25° C., and is preferably 20° C. The conversion time varies from 0.5 to 2 hours, depending on the operating conditions, but usually is about 1 hour. In order to avoid microbial contamination of the enzyme preparation, a stream of nitrogen is flowed through a bottom diffuser at about 0.01 vol/vol/min under a gentle agitation.

After the reaction is completed, determined by the conversion of not less than 97% of 3-thiolated glutaryl-7-ACA derivative or by the decrease of ammonium consumption rate to 2% of the initial consumption rate, the solution is filtered and the resin, in which glutaryl-7-ACA acylase is immobilised, is washed with, preferably 100 mM phosphate buffer pH 7.0.

The yield of 3-thiolated-7-ACA (compound III) after both enzymatic stages is about 94%. The latter compound is then recovered from the final solution by crystallisation at an acidic pH from 1.7 to about 5.5, depending on the isoelectric point of the final product, with inorganic acids such as hydrochloric, sulphuric or phosphoric, or by combining any of these acids with suitable organic solvents at different ratios.

The process of the invention is new and permits a good overall product yield, better quality (in terms of colour and purity), easy isolation, a continuous operation of the process and the reuse of the enzymes avoiding the poisoning by the remaining heterocyclic thiol after chemical reaction.

The process according to the present invention represents a surprising improvement over known three-stage processes for obtaining 3-heterocyclic thiolated-7-aminocephalosporanic acid because cephalosporin C in solution is first reacted with a heterocyclic thiol.

This can be conveniently done on a solution of cephalosporin C derived directly from the fermentation broth. The process thus avoids the need to crystallise cephalosporin C as a metal salt, and, at the same time, eliminates the need for the use and recovery of organic solvents. Further, it reduces yield losses on the overall recovery process for cephalosporin C. Since the 3 substituted derivatives are more stable in solution than the parent cephalosporin C, overall fermentation yields are effectively increased still further.

The highly selective removal of excess thiol allows compounds of formula I to be prepared at a very high purity level with very low levels (<0.2 mg/ml) of heterocyclic thiols present. The process has several important advantages. It allows compounds of formula I to be used as a substrate for enzymatic processes without the poisoning of the enzymes. As a result the enzymes may be used repeatedly. In addition the process does not require the use of toxic reagents or the need to isolate intermediates thereby providing a continuous process.

A highly selective removal procedure with the strong anion exchanger Amberlite IRA-400 (manufactured by Rohm and Haas) is utilised, which allows the compounds of formula I with very low levels (<0.2 mg/ml) of heterocyclic thiols present to be obtained.

The reaction of nucleophilic substitution in the 3'position is carried out in an aqueous medium, dissolving the heterocyclic thiol and any non-toxic cephalosporin C salt in water by addition of a basic compound which form a water soluble salt, such as alkali metal hydroxide, ammonium hydroxide or preferably alkali metal carbonate or bicarbonate. In general, in addition to salts produced as described above, any commercially available salt of cephalosporin C and of the heterocyclic thiols can be used in the process of this invention without changing the fundamentals of the process.

After dissolving the heterocyclic thiol and the cephalosporin C in separate reaction vessels or jointly, both reactants are mixed together in the same reactor, before or after heating the solution to a temperature from approximately 60° C. to 80° C. at a pH value of between 5.5 and 8.0.

Once the reaction starts, the temperature and pH are maintained preferably at approximately 65° C. and 6.0 respectively, for a period of time of approximately 1 hour to 4 hours.

The heterocyclic thiol/cephalosporin C molar ratio is an important variable in the yield of the reaction and has to be optimised for each heterocyclic thiol used. Molar ratios are between 1.0 and 4.0, preferably at a molar ratio of approximately 4.

It was found that at these molar ratios the cephalosporin C remains quite stable with low β-lactam ring degradation, compared to a cephalosporin C solution without the thiol, which is completely degraded within 40 min at 80° C.

Once the cephalosporin C level is below 2% of the initial amount, the reaction mixture is cooled to a temperature from about 2° C. to about 10° C., with or without acidification at a pH of from pH 3.0 to 5.5, preferably approximately 5.2, with strong mineral acids, such as hydrogen halides or oxy acids.

This acidification step gives in some cases, crystallisation of the heterocyclic thiol, with the concomitant possibility of reuse for a new reaction.

The resulting solution after the reaction with or without the acidifying step is subjected to subsequent purification by chromatography. Different resins and types of chromatography may be used on an industrial scale.

Several resins were tested grouped in four classes of resins based on adsorption, hydrophilic-hydrophobic interaction, cation exchange, and anion exchange. All resins tested based on adsorption (Amberlite XAD-761, Amberlite 7HP, Amberlite 16 HP and Amberlite XAD-4) gave similar results, the eluate containing from 22% to 38% of the heterocyclic thiol. The hydrophobic-hydrophilic interaction resin Sephadex LH-20 did not retain any thiol (<5%). A similar situation was found with the cation exchangers Amberlite® IRC-50, IR-120 and IR-200. However, anion exchangers were found to have the best binding capacity for heterocyclic thiols ranging from 57–60% in the case of a weak anion exchanger (Amberlite IRA-93).

It was found that a strong microporous (gel-type I) anion (base) exchange resin Amberlite IRA-400 having an 8% cross linking containing function trialkyl benzyl ammonium groups gave the highest binding of heterocyclic thiols (from 92–98%) and low binding of the 3'-position heterocyclic thiomethyl cephalosporin C derivative (from 2–15%, less than 15% for the first cycle and less than 5% for the following cycles).

Such a microporous resin offers certain advantages. They are less fragile, require less care in handling and possess higher loading capacities. As they have no discrete pores solute ions diffuse through the particle to interact with exchange sites. The total exchange capacity of the mentioned resin is in the order of 1,4 meq/ml.

It was surprisingly found that Amberlite IRA-400 has less binding capacity for 3-heterocyclic thiomethyl derivatives of cephalosporin C than for the same derivatives of glutaryl-7-ACA and 7-ACA. In fact the 3-heterocyclic thiomethyl derivative of glutaryl-7-ACA produced with MMTD binds at a level of 76.3% to the column. The same result is found with 3-heterocyclic thiomethyl derivative of 7-ACA, with MMTD, which binds at a level of 92.7% to the column. This unexpected behaviour of Amberlite IRA-400 with these three related β-lactam compounds appears to result from the presence of an ionisable amino group in the 5 position of the side chain of cephalosporin C compared with glutaryl-7-ACA and 7-ACA.

The removal of heterocyclic thiols by the process of the invention is particularly advantageous on an industrial scale as the elute of the column can be used for enzymation without isolation of the modified cephalosporin C and represents a new concept in the field of cephalosporin intermediates wherein the impurities are bound to the column and the β-lactam derivative is simply eluted by water.

Once the β-lactam derivative is eluted (less than 5% remains bound), the column is typically regenerated with a 1.5 N solution of a strong mineral acid, such as hydrogen halide containing variable amounts of an organic solvent, preferably 10–20% acetonitrile. When the concentration of the thiol in the eluate is higher than 0.2 mg/ml, a strong regeneration using 3 N HCl and 40% acetonitrile may be carried out. Alternatively, regeneration with successive NaOH and HCl solutions may be carried out.

After elution of the heterocyclic thiol, the thiol is concentrated and reused. The column is rinsed with deionised water to remove excess regenerant before the next cycle. The first bed volume of the rinse should be performed at the flow rate used for regeneration. The remainder is run at the adsorption flow rate.

The 3-thiolated derivative (TXC), has been found to be surprisingly good substrate, compared with unmodified cephalosporin C. The process of the present invention therefore provides an improved and more economical process for the preparation of cephalosporin C derivatives.

A second important aspect of the process of the invention is the use of enzymes in a re-usable form, either immobilised on a solid support or in the form of large stabilised crystals. This last requirement is important in producing a process to be operated on an industrial scale.

A further important advantage of the present invention is the ease of transferring the chemical solution after the removal and recovery of excess thiol to the first enzymatic reactor and from it to the second enzymatic reactor. This enables the process to be conducted continuously with a single liquid stream from cephalosporin C concentrate or prepared batch solution to 3-thiolated-7-ACA derivative, which is easy to crystallise compared with unmodified 7-ACA.

The following examples are meant to illustrate the invention without limitation as to its generality.

Examples 1 to 5 illustrate the preparation of 3-thiolated-7-ACA derivatives of formula I from cephalosporin C.

Examples 6 to 10 illustrate the preparation of 3-thiolated-7-ACA derivatives of formula III through the formation of 3-thiolated-glutaryl-7-ACA derivatives of formula I.

EXAMPLE 1

Preparation of 7-β-(5-amino-5-carboxypentanamido)-3-(5-methyl-1,3,4-thiadiazole-2-yl thiomethyl)-3-cephem-4-carboxylic acid (TDC)

To a glass-lined reactor containing 600 ml of deionised water, 31.73 g (0.24 moles) of 2-mercapto-5-methyl-1,3,4-thiadiazole (MMTD) were added and the reactor was heated with stirring to a temperature of about 65° C. The pH of the mixture was adjusted to pH of about 6.0 by the addition of about 10 g of sodium carbonate.

In a separate glass-lined flask, a solution of concentrated sodium cephalosporin C (98% purity by HPLC) was prepared by dissolving 33.23 g of sodium cephalosporin C (75% free acid, 0.06 moles) in 200 mL of water. When the MMTD was dissolved, the concentrated cephalosporin C solution was added and the mixture was stirred at approximately 65° C. for 240 minutes, controlling the reaction kinetic until the level of cephalosporin C was below 2%. The following reaction kinetics were found:

| Time (mins) | Cephalosporin C (moles) | TDC (moles) | MMTD (moles) |
|---|---|---|---|
| 0 | 0.06 | 0.00 | 0.24 |
| 120 | 0.01 | 0.039 | 0.20 |
| 240 | 0.0012 | 0.042 | 0.195 |

The reaction mixture was then cooled to approximately 4° C., where the crystallisation of the excess MMTD begins. The pH was acidified with stirring (150 rpm) to a pH 5.2 with 37% hydrochloride acid and left under slow stirring (50 rpm) for 60 minutes for the completion of crystallisation.

The precipitated MMTD was filtered and dried at 35° C. under vacuum. 23 g of recovered MMTD was obtained (purity 99% by HPLC) with a recovery yield of about 95%.

The filtrate (825 ml) containing 0.042 moles of the TDC and MMTD 0.016 moles was adjusted to pH 7.25 with 3 M ammonia and loaded onto an Amberlite IRA-400 column in chloride cycle (bed volume equal to 180 ml) covered with deionised water at flow rate 20 ml/min. Once loaded, the column was washed with deionised water (ca 100 ml) until 97% recovery of loaded TDC with a 94% purity by HPLC. The pH of the effluent was about 5.4 and was neutralised to 7.0 with 3 M ammonia. The remaining MMTD was 0.0009 moles (<0.2 mg/ml), which is less than 6% of the remaining MMTD after its crystallisation by decreasing the pH. With this low level of MMTD (<1% of the original MMTD after chemical reaction), enzymation of TDC is possible.

Typically the column is regenerated with 1 L of 1.5 M HCl containing 10% acetonitrile and rinsed free of the excess regeneration by washing with 2 liters of deionised water. When required (MMTD>0.2 mg/ml) the resin can be subjected to a strong regeneration using 1 liter of 3 M HCl with 40% acetonitrile.

To further characterise the TDC solution at pH 5.0, it was loaded onto a Amberlite XAD-2 adsorption column and the column was washed with water. After washing, the resin was eluted with water, and 25 ml portions were pooled. A fraction containing 98.5% TDC by HPLC was lyophylised and subjected to analysis:

Elemental Analysis for the product $C_{17} H_{20} N_5 O_6 S_3 \cdot 2 H_2O$ (TDC), calculated C 37.42; H 4.43; N 12.84; S 17.63; found 37.27; H 4.3; N 13.11; S 17.51.

$^1$H-NMR (DMSO/DCl) (δ ppm): 1.57 (m, 2H, —CH$_2$—); 1.63 (m, 2H, —CH$_2$—); 2.18 (m, 2H, —CH$_2$—); 2.64 (s, 3H, CH$_3$); 3.55, 373 (J=18 Hz, 2H, —CH$_2$—); 3.83 (t, 1H, —CH—); 4.18–4.46 (d, J=13 Hz, 2H, —CH$_2$—); 5.02 (d, J=3 Hz, 1H, C-6); 5.6 (d, J=3 Hz, 1H, C-7).

EXAMPLE 2

Comparative Example: Preparation of 7-β-(5-amino-5-carboxypentanamido)-3-(5-methyl-1,3,4-thiadiazole-2-yl thiomethyl)-3-cephem-4-carboxylic acid on different columns The TDC derivative was prepared as described in Example 1 and the filtrate containing it was loaded onto different types of resins.

The following data was obtained after washing with 100 ml of water in the first cycle of column usage:

| Resin | Type | Eluted TDC (%) | Eluted MMTD (%) |
|---|---|---|---|
| Amberlite IRA-400 | Strong anion exchanger | 86 | 2 |
| Diaion SA10A | Strong anion exchanger | 67 | 15 |
| Amberlite IRA93 | Weak anion exchanger | 87 | 45 |
| Amberlite IRC-50 | Weak cation exchanger | 93 | 92 |
| Amberlite IRC-200 | Strong cation exchanger | 73 | 98 |

-continued

| Resin | Type | Eluted TDC (%) | Eluted MMTD (%) |
|---|---|---|---|
| Amberlite XAD-761 | Adsorption | 86 | 22 |
| Amberlite XAD-7 HP | Adsorption | 77 | 23 |
| Amberlite XAD-16 HP | Adsorption | 75 | 35 |
| Amberlite XAD-4 | Adsorption | 68 | 25 |
| Amberlite XAD-1180 | Adsorption | 78 | 38 |
| Sephadex LH-20 | Hydrophobic hydrophilic | 98.5 | 95 |

Amberlite IRA-400 gave the best results. A high elution of TDC was observed with low elution of MMTD. Using other anion exchange columns higher amounts of MMTD were also eluted. The other anion exchangers showed a high dual binding of thiol and TDC.

EXAMPLE 3

Specificity of TDC for Amberlite IRA-400

The glutaryl-7-ACA derivative (TDG) and 7-ACA derivative (7-TDA) were prepared as in Example 1 using glutaryl-7-ACA and 7-ACA as starting material. The following data was obtained from the filtrate of the Amberlite IRA-400.

| Resin | Compound in the elute | TDG or TDA eluted (%) | MMTD eluted (%) |
|---|---|---|---|
| Amberlite IRA-400 | TDG | 23.7 | 3.0 |
| | TDA* | 7.3 | 1.4 |

*At pH 7.8 to avoid any precipitation of TDA into the column.

In contrast to TDC, both TDG and TDA appear to remain bound to the Amberlite IRA-400 as well as the MMTD.

EXAMPLE 4

Preparation of 7-β-(5-amino-5-carboxypentanamido)-3-[(1-methyl-1H-tetrazol-5-yl)-thiomethyl]-cephalosporanic acid (TZC)

To a glass-lined reactor containing 600 ml of deionised water 28.16 g (0.24 moles) of 5-mercapto-1-methyltetrazole (MMTZ) were added and the reactor was heated with stirring to a temperature of approximately 70° C. The pH of the mixture was adjusted to pH of approximately 5.7–5.8 by the addition of approximately 12 g of sodium carbonate.

In a separate glass-lined flask, a solution of concentrated sodium cephalosporin C was prepared by dissolving 33.23 g of sodium cephalosporin C (75% free acid, 0.06 moles purity 98% by HPLC) in 200 ml of water. When the MMTZ was dissolved, the concentrated cephalosporin C solution was added and the mixture was stirred at about 70° C. for 120 minutes, controlling the reaction kinetic until the level of cephalosporin C was below 3%.

| Time (minutes) | Cephalosporin C (moles) | TZC (moles) | MMTZ (moles) |
|---|---|---|---|
| 0 | 0.06 | 0 | 0.24 |
| 120 | 0.0017 | 0.040 | 0.19 |

The reaction mixture was cooled at about 4° C., but crystallisation of the excess of MMTZ did not start, even when the pH was decreased. The solution containing 0.04 moles of the TZC derivative from MMTZ and 0.19 moles of MMTZ was adjusted to pH 7.25 with 3 M ammonia and loaded onto an Amberlite IRA-400 column in chloride cycle (bed volume equal to 150 ml) covered with deionised water at flow rate 20 ml/min. After the first pass through the column the remaining MMTZ was higher than 13% of the initial (0.032 moles).

For this reason, the eluate was loaded onto another Amberlite IRA-400 (bed volume equal to 60 ml) column under the same conditions as described above to decrease the level of MMTZ.

Once loaded, the column was washed with deionised water (ca 90 ml) until 97% recovery of loaded TZC with a 87% purity by HPLC. The pH of the effluent was about 5.4 and was neutralised to pH 7.0 with 3 M ammonia. The remaining MMTZ concentration was 0.0013 moles, which is less than 1% of the original MMTZ after chemical reaction. With this low level of MMTZ, enzymation of the derivative is possible without poison the enzyme.

The columns were regenerated with 1 L of 1.5 M HCl containing 10% acetonitrile and rinsed free of the excess regeneration by washing with 2 liters of deionised water.

EXAMPLE 5

Preparation of 7-β-(5-amino-5-carboxypentanamido)-3-[(1,2,5,6-terahydro-2-methyl-5,6-dioxo-1,2,4-triazin-3-yl)-thiomethyl]-cephalosporanic acid (TZC)

To a glass-lined reactor containing 600 mL of deionised water 37.96 g (0.24 moles) of 2,5-dihydro-3-mercapto-2-methyl-5,6-dioxo-1,2,4-triazine (here below indicated as TTZ) were added and the reactor was heated with stirring to a temperature of approximately 75° C. The pH of the mixture was adjusted to pH of about 6.7 by the addition of approximately 12 g of sodium carbonate.

In a separate glass-lined flask, a solution of concentrated sodium cephalosporin C was prepared by dissolving 33.23 g of sodium cephalosporin C (75% free acid, 0.06 moles, purity 98% by HPLC) in 200 ml of water. When the TTZ was dissolved, the concentrated cephalosporin C solution was added and the mixture was stirred at about 75° C. for 75 minutes, controlling the reaction kinetic until the level of cephalosporin C was below 2%.

| Time (minutes) | Cephalosporin C (moles) | TTC (moles) | TTZ (moles) |
|---|---|---|---|
| 0 | 0.06 | 0 | 0.24 |
| 75 | 0.0011 | 0.036 | 0.19 |

The reaction mixture was cooled at about 4° C., but crystallisation of the excess of TTZ does not start, even when the pH was decreased. The solution containing the 0.036 moles of TTC and 0.19 moles of TTZ was adjusted to pH 7.25 with 3 M ammonia and loaded onto an Amberlite IRA-400 column in chloride cycle (bed volume equal to 209 ml) covered with deionised water at flow rate 20 ml/min. After the first column the remaining TTZ was 0.015 moles.

For this reason, the eluate was loaded onto another Amberlite IRA-400 column (with the same bed volume) under the same conditions as described above to decrease the level of TTZ.

Once loaded, the column was washed with deionised water (ca 120 ml) until 60% recovery of loaded TTC with a 90% purity by HPLC. The pH of the effluent was about 5.4 and was neutralised to pH 7.0 with 3 M ammonia. The remaining TTZ concentration was 0.00096 moles, which is less than 1% of the original TTZ after chemical reaction. With this level of TTZ, enzymation of the derivative is possible without poisoning the enzyme.

The columns were regenerated with 1 L of 1.5 M HCl containing 10% acetonitrile and rinsed free of the excess regeneration by washing with 2 liters of deionised water.

EXAMPLE 6

Synthesis of 7-amino-3-[(5-methyl-1,3,4-thiadiazol-2-yl)-thiomethyl]-cephalosporanic acid (TDA)

A filtrate (925 ml) from the strong anion exchanger Amberlite® IRA-400 from Example 1, containing 0.041 moles of 7β-(5-amino-5-carboxypentamido)-3-[(5-methyl-1,3,4-thiadiazole-2-yl)-thiomethyl]-cephalosporanic acid, hereinbelow indicated as TDC, with 94.4% purity (HPLC) and less than 0.2 mg/mL of 2-mercapto-5-methyl-1,3,4-thiadiazole (MMTD) was adjusted to pH 7.0 with 3 M ammonia.

The TDC solution was fed into a 1.5 liter stirred reactor with 82.5 g (30.3 Roche's Units/g) of wet immobilised D-amino acid oxidase available from Roche Molecular Biochemicals and produced as described in WO-A-9516773.

The conversion was performed at 20° C., 400 rpm and with an oxygen flow through a bottom diffuser of 0.1 vol/vol/min at 2 bar absolute pressure. The pH was titrated to pH 7.0 with 3 M ammonia by an autotitrator.

The conversion was controlled by HPLC an a reverse phase column Nucleosil 120 3-C18 125×8×4 mm the mobile phase was 20 mM acetate ammonium pH 5.5 containing 4% acetonitrile at 1 ml/min with a 260 nm detector. The TDC appeared at 7.0 minutes, the α-ketoadipyl-intermediate at 8.5 min and the TDG (the 3-thiolated glutaryl-7-ACA) at 11.5 min.

Representative samples of the reaction mixture except for the enzyme were taken and the results obtained are reported in the following table:

| Time (minutes) | TDC [%] conversion | TDK [%] production | TDG [%] production | TDA [%] production | side products [%] production |
|---|---|---|---|---|---|
| 0 | 0.00 | 0.00 | 0.00 | 0.00 | 0.00 |
| 10 | 30.20 | 2.04 | 25.49 | 0.00 | 0.30 |
| 100 | 98.49 | 2.94 | 94.69 | 0.00 | 0.86 |
| H₂O₂ titration | 98.60 | 0.00 | 97.71 | 0.00 | 0.89 |

When the conversion of TDC was higher than 98%, the reaction was stopped and the reaction solution was filtered off. The remaining biocatalyst was washed with 100 ml of 100 mM phosphate buffer pH 7.0. This latter volume was added to the first filtrate.

To transform the residual α-ketoadipyl-thiolated derivative (TDK) to TDG, the solution obtained was titrated with 1 M hydrogen peroxide to 35 ppm for 30 minutes at 25° C. The conversion was controlled by HPLC until maximal production of TDG (see above table). The purity after treatment was: 92.65% TDG and 7.34% of other β-lactams.

The residual hydrogen peroxide was removed by adding 10 μl of soluble *Corynebacterium glutamicum* catalase (650 kU, available from Roche Molecular Biochemicals) for 5 minutes.

The resulting TDG solution was adjusted to pH 8.0 with 3 M ammonia and transferred to a 1.5 L stirred reactor containing 57.08 g (87.6 Roche's Units/g) of wet immobilised glutaryl-7-ACA acylase (available from Roche Molecular Biochemicals). The conversion was performed at 20° C., 250 rpm and with a nitrogen flow through a bottom diffuser of 0.01 vol/vol/min at ambient pressure. The pH value was titrated to pH 8.0 with 3 M ammonia by an autotitrator. The conversion was controlled by HPLC with the same conditions as D-AAO reaction. The retention time for the product, 7-amino-3-[(5-methyl-1,3,4-thiadiazol-2-yl)-thiomethyl]-cephalosporanic acid (herebelow referred as TDA) was 7.2 minutes.

Representative samples of the reaction mixture were taken and the result obtained are shown in the following table:

| Time (minutes) | TDG [%] conversion | TDA [%] production | side products [%] production |
|---|---|---|---|
| 0 | 0.00 | 0.00 | 0.89 |
| 10 | 68.92 | 65.12 | 2.52 |
| 50 | 97.40 | 93.61 | 2.52 |

When the TDG conversion was higher than 97%, the reaction was stopped and the reaction solution was filtered off. The remaining enzyme was washed with 100 ml of 100 mM phosphate buffer pH 7.0 and the remaining catalyst was ready for reuse. This latter volume was added to the filtrate, containing TDA, and cooled to 10° C. The pH was adjusted to 5.2 by concentrated sulphuric acid and allowed to crystallise for 60 minutes under slow stirring.

The precipitate was filtered off and washed successively with 250 ml of 50% acetone/water and 100 ml of acetone, filtered again and dried at 35° C. under vacuum to obtain 13.91 g (K.F. 1.81%) of substantially pure 7-amino-3-[(methyl-1,3,4-thiadiazol-2-yl)-thiomethyl]-cephalosporanic acid, having an HPLC purity of 98.2% and a transmittance at 420 nm of 87 (determined as 1% solution in 2% NaHCO₃; 1 cm cell).

The overall yield from the starting cephalosporin C solution (24.92 activity grams of free acid) in this CEE process to TDA was 64.6%.

TDA $^1$H-NMR (DMSO/HCl) (δ ppm): 2.59 (s, 3H, —CH₃); 3.68 (broad s, 2H, —CH₂—); 4.2–4.48 (J=13.2 Hz, 2H, —CH₂—); 5.03 (d, J=4.8 Hz, 1H, C-6); 5.11 (d, J=4.8 Hz, 1H, C-7).

Elemental Analysis

Calculated for $C_{11}H_{12}N_4S_3O_3$: C:38.36%; H: 3.51%; S: 27.93%; N: 16.27%. Found: C:38.35%; H: 3.4%; S: 28.00%; N: 16.04%.

EXAMPLE 7

Effect of Heterocyclic Thiol Present in TDC Solution in the Reuses of the Enzyme To show the poisonous effect of remaining heterocyclic thiol in the two-step enzymation of TDC, TDC was used with and without heterocyclic thiol removal by chromatography in a strong anion exchanger Amberlite® IRA-400. The level of MMTD after crystallisation step was 2.56 mg/ml. After the chromatographic step onto an Amberlite® IRA-400 strong anion exchanger, the amount of MMTD was less than 0.2 mg/mL, which represents less than 1% of the original MMTD used.

The following table shows how without the chromatographic step the length of the D-amino acid oxidase time doubles after 4 cycles, whereas it remains the same ($\approx 100$ minutes), after 12 cycles in the case of TDC with traces of MMTD.

| CYCLE | D-amino acid oxidase T(min) | glutaryl-7-ACA acylase T(min) |
|---|---|---|
| Without chromatographic step | | |
| 1 | 100 | 70 |
| 2 | 150 | 50 |
| 3 | 150 | 60 |
| 4 | 230 | 60 |
| With chromatographic step | | |
| 1 | 90 | 60 |
| 2 | 90 | 60 |
| 3 | 100 | 50 |
| 4 | 90 | 50 |
| 5 | 100 | 50 |
| 6 | 90 | 50 |
| 7 | 100 | 50 |
| 8 | 100 | 50 |
| 9 | 100 | 50 |
| 10 | 100 | 50 |
| 11 | 100 | 50 |
| 12 | 100 | 50 |

As regards, the second enzyme glutaryl-7-ACA-acylase, it seems that the hydrogen peroxide produced and added after the first reaction destroys traces of MMTD, preserving its catalytic activity with reaction times of about 50 minutes.

EXAMPLE 8

Synthesis of 7-amino-3-[(1-methyl-1H-tetrazol-5-yl)-thiomethyl]-cephalosporanic acid (TZA)

A filtrate (1000 ml) from the strong anion exchanger Amberlite ® IRA-400 from Example 4, containing 0.039 moles of 7-(5'-amidoadipamido)-3-[(1-methyl-1H-tetrazol-5-yl)-thiomethyl]-cephalosporanic acid (TZC) with 91.3% purity (HPLC) and less than 0.2 mg/ml of 5-mercapto-1-methyltetrazole (MMTZ) was adjusted to pH 7.25 with 3 M ammonia.

The TZC solution was fed into a 1.5 liter stirred reactor with 82.5 g (30.3 Roche's Units/g) of wet immobilised D-amino acid oxidase available from Roche Molecular Biochemicals and produced as disclosed in WO-A-9516773.

The conversion was performed at 20° C., 400 rpm and with an oxygen flow through a bottom diffuser of 0.1 vol/vol/min at 2 bar absolute pressure. The pH was titrated to pH 7.25 with 3 M ammonia by an autotitrator.

The conversion was controlled by HPLC an a reverse phase column Nucleosil 120 3-C18 125×8×4 mm; the mobile phase was 20 mM ammonium acetate pH 5.5 with 4% acetonitrile at 1 ml/min with a 260 nm detector. The TZC appeared at 3.0 minutes, the α-ketoadipyl-intermediate at 3.6 min and the TZG at 4.6 min (the 3-thiolated glutaryl-7-ACA).

Representative samples of the reaction mixture except for the enzyme were taken and the result obtained are reported in the following table:

| Time (minutes) | TZC [%] conversion | TZK [%] production | TZG [%] production | TZA [%] production | side products [%] production |
|---|---|---|---|---|---|
| 0 | 0.00 | 0.00 | 0.00 | 0.00 | 0.00 |
| 10 | 73.98 | 6.49 | 66.02 | 0.00 | 0.30 |
| 35 | 100.00 | 4.26 | 91.28 | 0.00 | 2.12 |
| $H_2O_2$ titration | 100.00 | 0.00 | 98.17 | 0.00 | 1.83 |

When the conversion of TZC was higher than 99%, the reaction was stopped and the reaction solution was filtered off. The remaining biocatalyst was washed with 100 ml of 100 mM phosphate buffer pH 7.0. This latter volume was added to the first filtrate.

To transform the residual α-keto adipyl-thiolated derivate (TZK) to TZG, the solution obtained was titrated with 1 M hydrogen peroxide to 35 ppm for 30 minutes at 25° C. the conversion was controlled by HPLC (see above table). The purity after the treatment was: 89.45% TZG and 10.55% of other β-lactams.

The residual hydrogen peroxide was removed by adding 10 μl of soluble *Corynebacterium glutamicum* catalase (650 kU, available from Roche Molecular Biochemicals) for 5 minutes.

The resulting TZG solution was adjusted to pH 8.0 with 3 M ammonia and transferred to a 1.5 L stirred reactor contained 57.08 g (87.6 Roche's Units/g) of wet immobilised glutaryl-7-ACA acylase (available from Roche Molecular Biochemicals). The conversion was performed at 20° C., 250 rpm and with a nitrogen flow through a bottom diffuser of 0.01 vol/vol/min at ambient pressure. The pH value was titrated to pH 8.0 with ammonia by an autotitrator. The conversion was controlled by HPLC with the same conditions as D-AAO reaction. The retention times for the product, 7-amino-3-[(5-methyl-1,3,4-thiadiazol-2-yl)-thiomethyl]-cephalosporanic acid (herein-below referred as TZA) was 3.2 minutes.

Representative samples of the reaction mixture were taken and the result obtained are shown in the following table

| Time (minutes) | TZK [%] conversion | TZG [%] conversion | TZA [%] production | side products [%] production |
|---|---|---|---|---|
| 0 | 0.00 | 0.00 | 0.00 | 1.83 |
| 10 | 0.00 | 73.08 | 69.72 | 3.36 |
| 45 | 0.00 | 100.00 | 95.12 | 4.88 |

When the TZG conversion was higher than 99%, the reaction was stopped and the reaction solution was filtered off. The remaining enzyme was washed with 100 ml of 100 mM phosphate buffer pH 7.0 and the remaining catalyst was ready for reuse. This latter volume was added to the filtrate, containing TZA, and cooled to 10° C. The pH was adjusted to 5.2 by concentrated sulphuric acid and allowed to crystallise for 60 minutes under slow stirring.

The precipitate was filtered off and washed successively with 250 mL of 50% acetone/water and 100 ml of acetone, filtered again and dried at 35° C. under vacuum to obtain 9.94 g (K. F. 1.4%) of substantially pure 7-amino-3-[(methyl-1,3,4-thiadiazol-2-yl)-thiomethyl]-cephalosporanic acid, having a HPLC purity of 96.60%.

The overall yield from the starting cephalosporin C solution (24.92 activity grams of free acid) in this ECC process to TZA was 48.05%.

TZA $^1$H-NMR ($D_2O/Na_2CO_3$) (δ ppm): 3.45–3.78 (J=17.7 Hz, 2H, —$CH_2$—); 4.01–4.3 (J=13.2 Hz, 2H, —$CH_2$—); 4.03 (s, 3H, —$CH_3$); 4.72 (d, J=4.8 Hz, 1H, C-6); 5.00 (d, J=4.8 Hz, 1H, C-7).

EXAMPLE 9

Effect of Heterocyclic Thiol Present in TZC Solution in the Reuses of the Enzyme To show the poisonous effect of remaining heterocyclic thiol in the two-step enzymation of TZC, TZC was used with and without heterocyclic thiol removal by chromatography in a strong anion exchanger Amberlite® IRA-400. The level of MMTZ after chemical reaction step was 27.6 mg/ml After the chromatographic step onto an Amberlite® IRA-400 strong anion exchanger was 0.2 mg/ml, which represent less than 1% of MMTZ used.

The following table shows how without the two chromatographic steps, the length of the D-amino acid oxidase reaction increased a little in two cycles, but dramatically affected the glutaryl-7-ACA acylase, which was unable to finish the second reaction in the second cycle.

| CYCLE | D-amino acid oxidase T(min) | glutaryl-7-ACA acylase T(min) |
|---|---|---|
| Without chromatographic step | | |
| 1 | 100 | >110 |
| 2 | 120 | >>110 |
| With chromatagraphic step | | |
| 1 | 45 | 45 |
| 2 | 35 | 45 |
| 3 | 35 | 40 |
| 4 | 40 | 48 |
| 5 | 45 | 48 |

However, the time of the cycles with chromatographic step, for both enzymes remained about the same in the five cycles presented in above table. This clearly shows the need of thiol removal for the stability of the enzymes.

EXAMPLE 10

Preparation of 7-amino-3-[(1,2,5,6-tetrahydro-2-methyl-5,6-dioxo-1,2,4-triazin-3-yl)-thiomethyl]-cephalosporanic acid (TTA)

A filtrate (1000 ml) from the strong anion exchanger Amberlite® IRA-400 from Example 5, containing 0.032 moles of 7β-(5-amino5-carboxypentamido)-3-[(1,2,5,6-terahydro-2-methyl-5,6-dioxo-1,2,4-triazin-3-yl)-thiomethyl]-cephalosporanic acid, hereinbelow indicated as TTC) with 88% purity (HPLC) and less than 0.2 mg/ml of 2,5-dihydro-3-mercapto-2-methyl-5,6-dioxo-1,2,4-triazine (TTZ) was adjusted to pH 7.25 with 3 M ammonia.

The TTC solution was fed into a 1,5 liter stirred reactor with 82.5 g (30.3 Roche's Units/g) of wet immobilised D-amino acid oxidase available from Roche Molecular Biochemicals and produced as disclosed in WO 95/16773.

The conversion was performed at 20° C., 400 rpm and with an oxygen flow through a bottom diffuser of 0.1 vol/vol/min at 2 bar absolute pressure. The pH was titrated to pH 7.25 with 3 M ammonia by an autotitrator.

The conversion was controlled by HPLC an a reverse phase column Nucleosil 100-5 C18 250×8×4.6 mm; the mobile phase was 25% methanol in 10 mM tetrabutylammonium hydrogen sulfate and 15 mM potassium dihydrogen phosphate at 1 ml/min with a 260 nm detector. The TTC appeared at 4.3 minutes, the α-ketoadipyl-intermediated at 6.8 min and the 3-thiolated glutaryl-7-ACA (TTG) at 8.2 min.

Representative samples of the reaction mixture except for the enzyme were taken and the result obtained are reported in the following table:

| Time (minutes) | TTC [%] conversion | TTK [%] production | TTG [%] production | TTA [%] production | side products [%] production |
|---|---|---|---|---|---|
| 0 | 0.00 | 0.00 | 0.00 | 0.00 | 0.00 |
| 40 | 75.43 | 1.80 | 66.67 | 0.00 | 5.21 |
| 90 | 97.60 | 2.67 | 88.54 | 0.00 | 6.39 |
| $H_2O_2$ titration | 97.60 | 0 | 90.96 | 0.00 | 6.5 |

When the conversion of TTC was higher than 97%, the reaction was stopped and the reaction solution was filtered off. The remaining biocatalyst was washed with 100 ml of 100 mM phosphate buffer pH 7.0. This latter volume was added to the first filtrate.

To transform the residual α-ketoadipyl-thiolated derivative (TTK) to TTG, the solution obtained was titrated with 1 M hydrogen peroxide to 35 ppm for 30 minutes at 25° C. The conversion was controlled by HPLC (see above table). The purity after of treatment was: 80.77% TTG and 19.23% of other β-lactams.

The residual hydrogen peroxide was removed by adding 10 μl of soluble *Corynebacterium glutamicum* catalase (650 kU, available from Roche Molecular Biochemicals) for 5 minutes.

The resulting TTG solution was adjusted to pH 8.0 with 3 M ammonia and transferred to a 1,5 L stirred reactor contained 57.08 g (87.6 Roche's Units/g) of wet immobilised glutaryl-7-ACA acylase (available from Roche Molecular Biochemicals). The conversion was performed at 20° C., 250 rpm and with a nitrogen flow through a bottom diffuser of 0.01 vol/vol/min at ambient pressure. The pH value was titrated to pH 8.0 with ammonia by an autotitrator.

The conversion was controlled by HPLC with the same conditions as D-AAO reaction. The retention times for the product, 7-(5'-amidoadipamido)-3-[(1,2,5,6-terahydro-2-methyl-5,6-dioxo-1,2,4-triazin-3-yl)-thiomethyl]-cephalosporanic acid (TTA) was 5.2 minutes.

Representative samples of the reaction mixture were taken and the result obtained are shown in the following table:

| Time (minutes) | TTK [%] conversion | TTG [%] conversion | TTA [%] production | side products [%] production |
|---|---|---|---|---|
| 0 | 0 | 0.00 | 0.00 | 6.39 |
| 10 | 0 | 94.33 | 84.49 | 7.13 |
| 50 | 0 | 100.00 | 89.09 | 7.64 |

When the TTG conversion was higher than 99%, the reaction was stopped and the reaction solution was filtered off. The remaining enzyme was washed with 100 mL of phosphate buffer pH 7.0 and the remaining catalyst was ready for reuse. This latter volume was added to the filtrate, containing TTA, and cooled to 10° C. The pH was adjusted to 4.2 by concentrated hydrochloric acid and allowed to crystallise for 60 minutes under slow stirring.

The precipitate was filtered off and washed successively with 250 ml of 50% acetone/water and 100 ml of acetone, filtered again and dried at 40° C. under vacuum to obtain 8.53 g (K.F. 5.95%) of substantially pure 7-(5'-amidoadipamido)-3-[(1,2,5,6-terahydro-2-methyl-5,6-dioxo-1,2,4-triazin-3-yl)-thiomethyl]-cephalosporanic acid, having an HPLC purity of 98.28%.

The overall yield from the starting cephalosporin C solution (24.92 activity grams of free acid) in this ECC process to TTA was 40.01%.

TTA $^1$H-NMR (D$_2$O/Na$_2$CO$_3$) (δ ppm): 3.43–3.7 (J=17.7 Hz, 2H, —CH$_2$—); 3.63 (s, 3H, —CH$_3$); 4.02–4.33 (J=13.8 Hz, 2H, —CH$_2$—); 4.73 (d, J=4.5 Hz, 1H, C-6); 5.02 (d, J=4.5 Hz, 1H, C-7).

The invention is not limited to the embodiments hereinbefore described which may be varied in detail.

What is claimed is:

1. An enzymatic process for preparing 3-thiolated 7-aminocephalosporanic acid derivatives comprising the steps:

enzymatically converting a 3-thiolated cephalosporin C of the formula I:

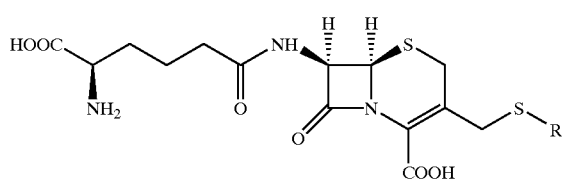

(I)

to form a 3-thiolated -glutaryl-7-ACA of the formula II

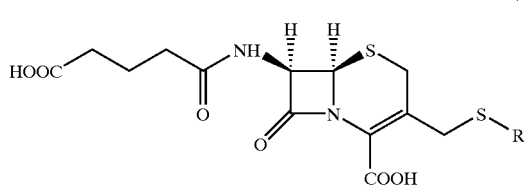

(II)

and enzymatically converting a compound of formula II to form a 3-thiolated-7-ACA of the formula III

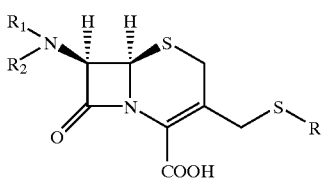

(III)

wherein R is a heterocyclic group comprising at least one nitrogen atom and R$_1$ and R$_2$ are both hydrogen atoms or one of them is a hydrogen atom and the other is an acyl donor.

2. A process as claimed in claim 1 wherein the 3-thiolated cephalosporin C of formula I is converted into a 3-thiolated -glutaryl-7-ACA of the formula II by:

reacting a compound of formula I with immobilised D-Amino acid oxidase in the presence of molecular oxygen;

separating the supported enzyme from the aqueous reaction mixture; and adding hydrogen peroxide to convert the 3-thiolated-α-ketoadipyl cephalosporanic acid into a compound of formula II.

3. A process as claimed in claim 2 wherein the compound of formula I is reacted with immobilised D-Amino acid oxidase at a pressure of about 2 bar absolute, a pH of from 6.0 to 8.0, and a temperature of from 20° C. to 30° C. for a period of from 0.5 to 3 hours.

4. A process as claimed in claim 2 including the step of washing the supported enzyme with a concentrated salt solution and adding hydrogen peroxide preferably in an amount equivalent to 30 to 50 ppm to the solution thus formed.

5. A process as claimed in claim 1 comprising the step of eliminating excess hydrogen peroxide from the solution, preferably by adding a catalyst to the solution.

6. A process as claimed in claim 5 wherein the excess hydrogen peroxide is removed by adding catalase to the solution.

7. A process as claimed in claim 1 wherein a compound of formula II is converted into a compound of formula III by contacting a compound of formula II with immobilised glutaryl-7-ACA acylase.

8. A process as claimed in claim 7 wherein the reaction to form a compound of formula III from a compound of formula II is carried out at ambient pressure, at a pH of from 6.0 to 8.5 and at a temperature of from 20° C. to 35° C., for a period of from 0.5 to 3 hours under an inert atmosphere.

9. A process as claimed in claim 7 wherein the compound of formula III is precipitated by acidifying the reaction medium and the precipitate thus formed is subsequently washed and dried.

10. A process as claimed in claim 1 wherein the enzymes are immobilised using a suitable cross-linker agent in a suitable solid support.

11. A process as claimed in claim 10 wherein the enzymes are in the form of crystals of a size suitable for use as a biocatalyst.

12. A process as claimed in claim 1 wherein the enzymatic processes are carried out while maintaining the enzyme in dispersion in an aqueous substrate solution.

13. A process as claimed in claim 1 wherein the or each enzymatic process is carried out in a column.

14. A process as claimed in claim 1 including the step of recovering the enzyme for reuse.

15. A process as claimed in claim 1 wherein crystallisation of a compound of formula III is carried out at an acidic pH.

16. A process as claimed in claim 1 wherein the enzymatic conversion of a 3 thiolated cephalosporin C of the formula I to form a 3 thiolated-7-ACA of the formula III is carried out in one pot.

17. A process as claimed in claim 1 wherein R is a heterocyclic group comprising at least one nitrogen atom and optionally a sulphur or oxygen atom.

18. A process as claimed in claim 1 wherein R is a heterocyclic group selected from any one or more of the group comprising thienyl, diazolyl, tetrazolyl, thiazolyl, triazinyl, oxazolyl, oxadiazolyl, pyridyl, pirimidinyl, benzo thiazolyl, benzimidazolyl, benzoxazolyl, or any derivative thereof, preferably 5-methyl-1,3,4-thiadiazol-2-yl, 1-methyl-1H-tetrazol-5-yl or 1,2,5,6-tetrahydro-2-methyl-5,6-dioxo-1,2,4-triazin-3-yl.

19. A process as claimed in claim 1, wherein compounds of formula I are in a solid form or in the form of a non-toxic salt thereof.

\* \* \* \* \*